US00PP26183P3

(12) United States Plant Patent
Dirr et al.

(10) Patent No.: US PP26,183 P3
(45) Date of Patent: Dec. 1, 2015

(54) ***LAGERSTROEMIA* PLANT NAMED 'PIILAG-VI'**

(50) Latin Name: ***Lagerstroemia* hybrid**
Varietal Denomination: PIILAG-VI

(71) Applicants: Michael A. Dirr, Bogart, GA (US); Joshua H. Kardos, Watkinsville, GA (US)

(72) Inventors: Michael A. Dirr, Bogart, GA (US); Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 121 days.

(21) Appl. No.: 13/998,271

(22) Filed: Oct. 17, 2013

(65) Prior Publication Data

US 2014/0283249 P1 Sep. 18, 2014

Related U.S. Application Data

(60) Provisional application No. 61/785,058, filed on Mar. 14, 2013.

(51) Int. Cl.
*A01H 5/00* (2006.01)
*A01H 5/02* (2006.01)

(52) U.S. Cl.
USPC ..... Plt./252
CPC ..... *A01H 5/02* (2013.01)

(58) Field of Classification Search
USPC ..... Plt./252
See application file for complete search history.

*Primary Examiner* — Susan McCormick Ewoldt
(74) *Attorney, Agent, or Firm* — Lathrop & Gage LLP

(57) ABSTRACT

A new and distinct cultivar of *Lagerstroemia* plant named 'PIILAG-VI', characterized by its compact, rounded to upright, intermediate growth habit, orange-red new growth, dark green mature foliage, orange-red young stems, bright red flowers, ability to rebloom in about 5-6 weeks if old flowers are removed, and resistance to powdery mildew and *Cercospora* leaf spot.

3 Drawing Sheets

Genus and species of plant claimed: *Lagerstroemia* Hybrid.

Variety denomination: 'PIILAG-VI'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'PIILAG-VI'. 'PIILAG-VI' is grown primarily as an ornamental for landscape use and for use as a potted plant.

'PIILAG-VI' originated from an open-pollination of *Lagerstroemia* 'PIILAG-III' (U.S. Plant Pat. No. 23,178) growing in Watkinsville, Ga. in 2008. The cultivar 'PIILAG-VI' originated and was selected in a cultivated environment in Watkinsville, Ga. from the progeny of this open-pollination by continued evaluation for growth habit and foliage and flower characteristics.

Asexual reproduction of 'PIILAG-VI' by stem cuttings in Watkinsville, Ga. since 2010 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG-VI' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-VI'. These characteristics in combination distinguish 'PIILAG-VI' as a new and distinct cultivar, unique from all other cultivars known to the inventor: 1. Compact, rounded to upright, intermediate growth habit; 2. Orange-red new growth; 3. Dark green mature foliage; 4. Orange-red young stems; 5. Bright red flowers; 6. Ability to rebloom in about 5-6 weeks if old flowers are removed; 7. Resistance to powdery mildew and *Cercospora* leaf spot.

'PIILAG-VI' is distinguished from its female parent, 'PIILAG-III', by its growth habit, foliage color and disease resistance. 'PIILAG-VI' has a compact, rounded to upright, intermediate growth habit, orange-red new growth, and improved resistance to *Cercospora* leaf spot, whereas 'PIILAG-III' has a compact, upright, intermediate growth habit, red-purple new growth, and moderate resistance to *Cercospora* leaf spot.

'PIILAG-VI' can be compared to the cultivar 'PIILAG B5' (U.S. Plant Pat. No. 25,476), but differs in the following characteristics. 'PIILAG-VI' has an overall smaller rounded to upright growth habit and brighter orange-red new growth and stems, whereas 'PIILAG B5' has an overall larger upright growth habit and darker red new growth and stems.

BRIEF DESCRIPTION OF THE DRAWINGS

The accompanying color photographs illustrate the flower and foliage characteristics and the overall appearance of 'PIILAG-VI', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
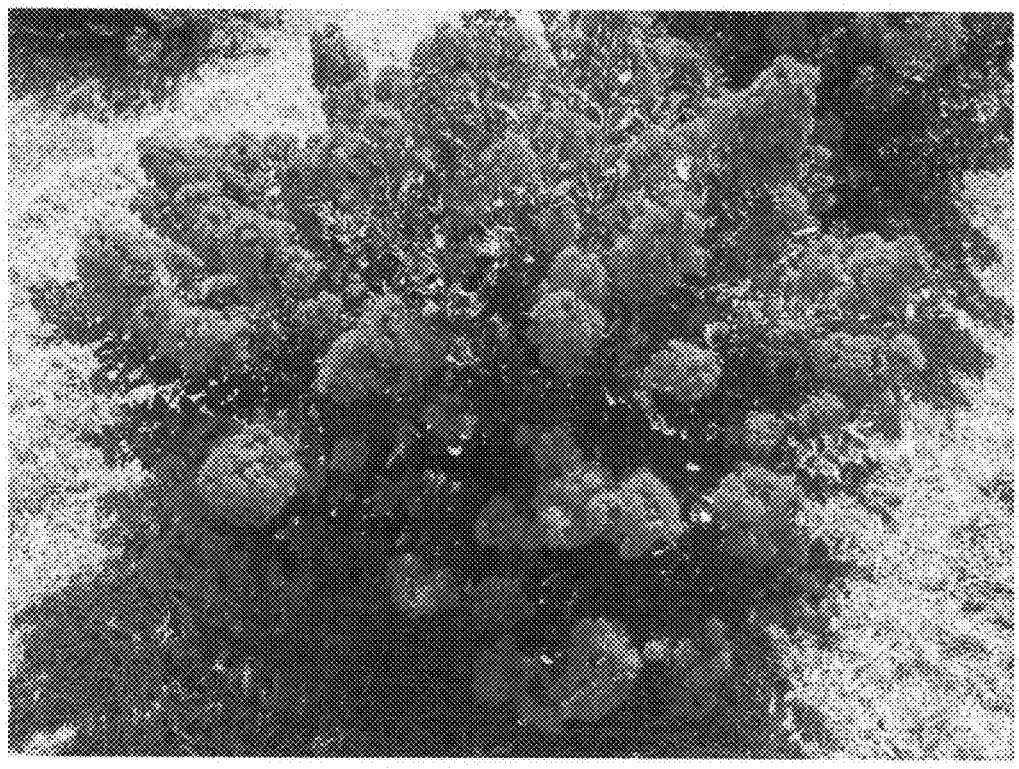
FIG. 1 illustrates the overall appearance of a plant of 'PIILAG-VI' planted in the ground.
Figure 2:
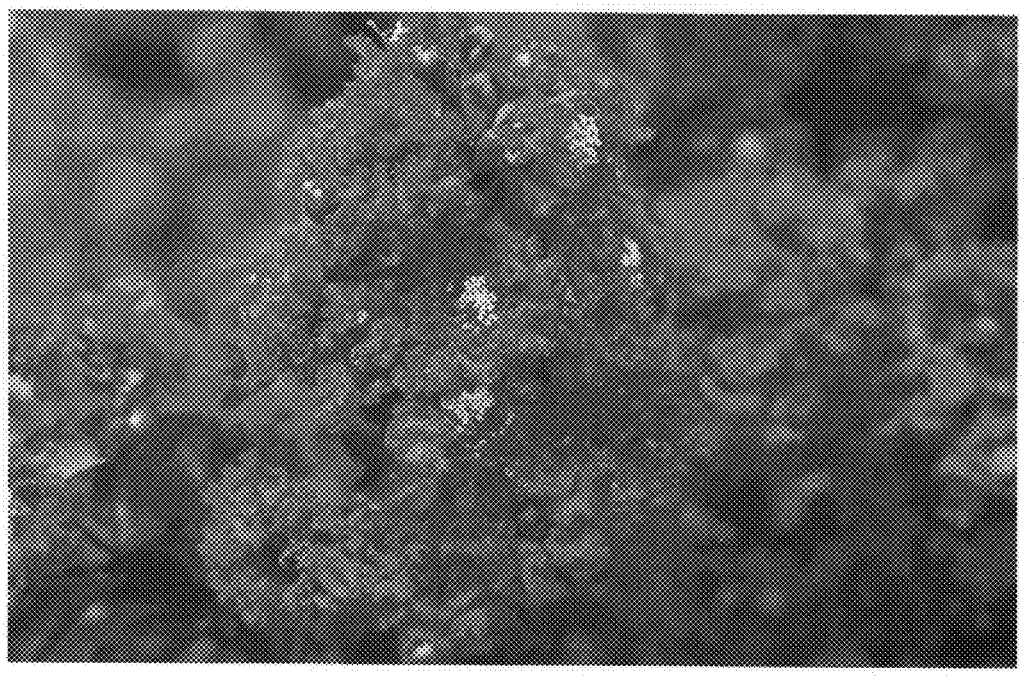
FIG. 2 illustrates a close-up view of the flowers of 'PIILAG-VI'.
Figure 3:
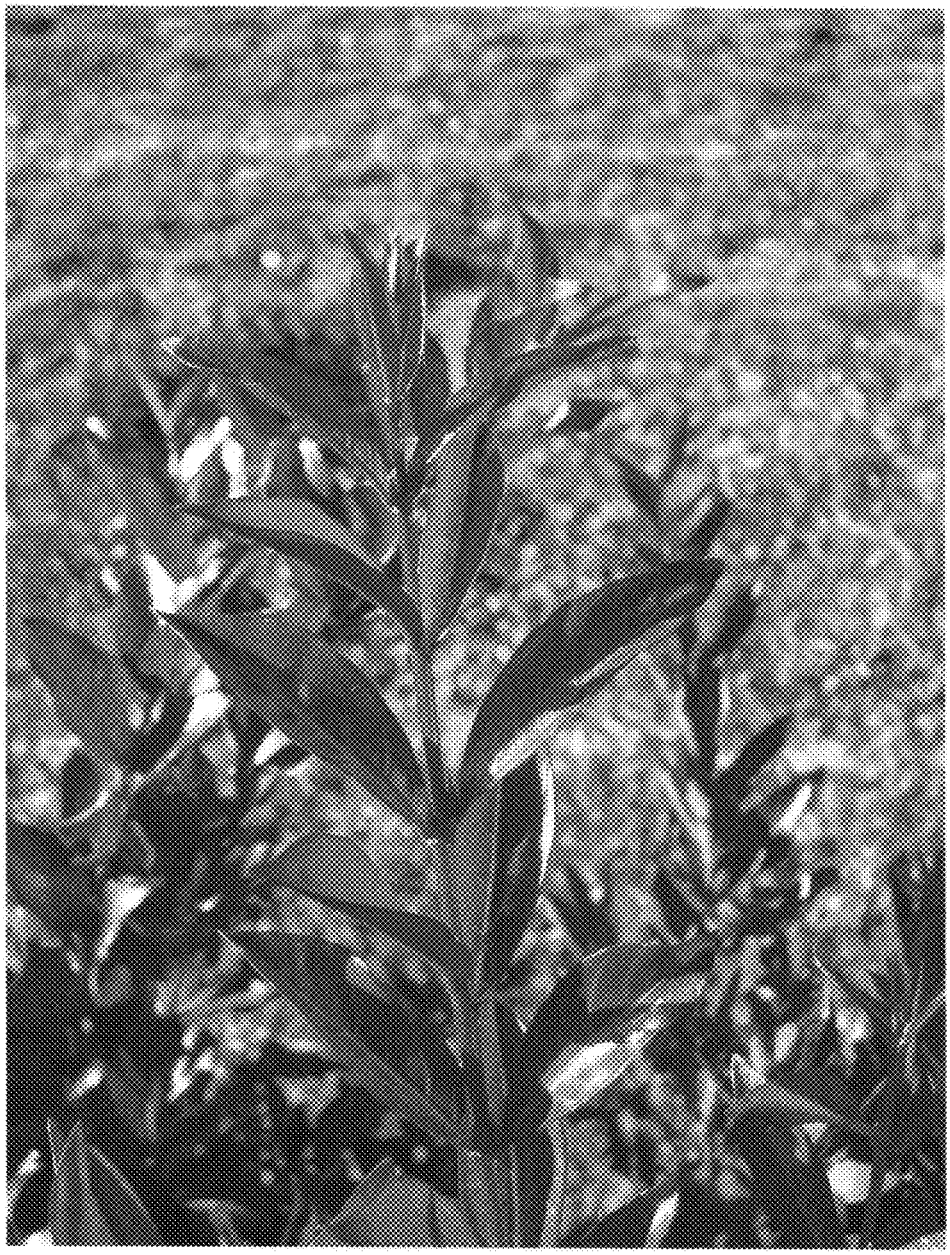
FIG. 3 illustrates a close-up view of the new growth of 'PIILAG-VI'.

In the following description, color references are made to The Royal Horticultural Society Colour Chart, 2007 Edition, except where general terms of ordinary dictionary significance are used. Plants used for the description were approximately two-years-old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-VI'.

Parentage:

*Female, or seed, parent.*—*Lagerstroemia* 'PIILAG-III' (U.S. Plant Pat. No. 23,178).

*Male, or pollen parent.*—Unknown (open-pollinated).

Propagation: Terminal cuttings.

Time to initiate roots, summer: About 21 days at 32° C.

Plant description: Deciduous flowering shrub; compact, rounded to upright, intermediate growth habit. Freely branching; pruning enhances lateral branch development.

*Root description.*—Numerous, fine, fibrous and well-branched.

*Plant size.*—The original plant, now about five-years-old in the ground, is about 132 cm high from the soil level to the top of the inflorescences and about 118 cm wide. First year stems have a diameter of about 2.5 mm. Shape: squarish. Second year and older stems have a diameter of about 3.5 mm or more. Shape: round.

*Trunk diameter.*—2.6 cm at the soil line. Color: 199D.

*Internode length.*—About 1.4 cm.

*Strength.*—Flexible when young, easily broken once mature.

*First year stem color* (*young*).—42B. Color (woody): 200C.

*Second year and older stem color.*—N199B.

*Bark.*—Exfoliates in strips beginning on second or third year stems.

Vegetative buds: Sub-opposite to alternate in arrangement, imbricate, conical, with no pubescence.

*Color.*—183C.

*Size.*—About 3 mm in length and 2 mm in width.

Foliage description:

*Arrangement.*—Sub-opposite to alternate, simple.

*Length.*—About 5.2 cm.

*Width.*—About 2.6 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper surface*).—183A.

*Venation color of emerging foliage* (*lower surface*).—178B.

*Venation color of fully expanded foliage* (*upper surface*).—178A at the base, changing to 174C at the apex.

*Venation color of fully expanded foliage* (*lower surface*).—174B.

*Color in developing foliage* (*upper and lower surfaces*).—42B.

*Color in mature foliage* (*upper surface*).—147A.

*Color in mature foliage* (*lower surface*).—146B.

*Color of the leaf margin of mature foliage* (*upper and lower surfaces*).—N186C.

*Petiole length.*—About 1.5 mm.

*Petiole diameter.*—About 1 mm.

*Petiole color* (*upper and lower surfaces*).—178A.

*Pubescence.*—None.

Flower description: Flowers are produced from about June to September in Watkinsville, Ga. If the plants are dead-headed, or the old flowers removed, they will rebloom in about 8-10 weeks. An inflorescence is showy for about two weeks, and individual flowers last about one day and are self-cleaning.

*Inflorescence type.*—Terminal panicle.

*Inflorescence length.*—About 11.7 cm.

*Inflorescence width.*—About 9.6 cm. Panicle contains between 30-50 flower buds and flowers.

*Peduncle.*—About 9.5 cm in length, about 2 mm in diameter, color is 181A, and no pubescence.

*Individual flowers.*—About 2.2 cm in height and 3.2 cm in diameter.

*Flower buds.*—Length: about 8 mm; Diameter: about 8 mm; Color: 46C. Unopened flower buds are globose with six distinct lines of dehiscence where they split to reveal the petals.

*Pedicels.*—About 8 mm in length, 44B in color, and no pubescence.

*Calyx.*—Consists of 6 fused sepals with acute apices and 176B in color. The calyx is about 9 mm in length, about 9 cm in diameter, 178B in color, and no pubescence.

Petals:

*Arrangement/appearance.*—Usually 6 per flower.

*Petal length.*—About 1.5 cm.

*Petal width.*—About 1.3 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are 46A.

Stamens:

*Quantity/arrangement.*—About 25 to 30 short stamens clustered in the center, about 8 mm long, filament color is 37C, and anther color is 13A. The short stamens are surrounded by 6 longer stamens, about 1.4 cm long, filament color is 44C, and anther color is 13A. The stamens are not pubescent. Pollen: produced in moderate quantities and is 7B in color on all stamens.

Pistils:

*Quantity.*—One superior pistil per flower.

*Pubescence.*—None.

*Pistil length.*—About 1.9 cm in length.

*Stigma shape.*—Round, about 1 mm in diameter.

*Stigma color.*—144B.

*Style color.*—41C and about 1.4 cm in length.

*Ovary color.*—10B and about 2.5 mm in diameter.

Fruit:

*Type/appearance.*—Six-valved, dehiscent, broad ellipsoidal capsule.

*Length.*—About 8 mm.

*Diameter.*—About 8 mm.

*Immature color.*—144A.

*Mature color.*—200C. Each capsule contains many seeds that are about 5 mm long, 3 mm wide, and 200C in color.

Disease/pest resistance: Plants of 'PIILAG-VI' grown in field and container trials have exhibited resistance to powdery mildew and *Cercospora* leaf spot. 'PIILAG-VI' is cold hardy in USDA Cold Hardiness Zones 6-9.

We claim:

1. A new and distinct *Lagerstroemia* plant named 'PIILAG-VI', as illustrated and described herein.

* * * * *